United States Patent
Iwai et al.

(10) Patent No.: US 9,488,590 B2
(45) Date of Patent: Nov. 8, 2016

(54) METHOD FOR EVALUATING COSMETIC FOR EFFECTIVENESS IN IMPROVING WRINKLES

(71) Applicant: SHISEIDO COMPANY, LTD., Chuo-ku, Tokyo (JP)

(72) Inventors: Ichiro Iwai, Kanagawa (JP); Yusuke Hara, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 14/388,542

(22) PCT Filed: Mar. 6, 2013

(86) PCT No.: PCT/JP2013/056174
§ 371 (c)(1),
(2) Date: Sep. 26, 2014

(87) PCT Pub. No.: WO2013/146151
PCT Pub. Date: Oct. 3, 2013

(65) Prior Publication Data
US 2015/0168308 A1    Jun. 18, 2015

(30) Foreign Application Priority Data

Mar. 27, 2012 (JP) ................. 2012-071065

(51) Int. Cl.
    *G06K 9/00*      (2006.01)
    *G01N 21/88*      (2006.01)
    (Continued)

(52) U.S. Cl.
CPC ............. *G01N 21/8803* (2013.01); *A61K 8/34* (2013.01); *A61K 8/345* (2013.01); *A61K 8/365* (2013.01); *A61K 8/86* (2013.01); *A61Q 19/08* (2013.01); *G01N 21/8851* (2013.01); *G01N 33/5088* (2013.01); *G06K 7/0004* (2013.01); *G06K 9/46* (2013.01); *G01N 2201/12* (2013.01)

(58) Field of Classification Search
CPC ..................... G01N 21/8803; G01N 21/8851; G01N 2201/12; G06T 7/0004; G06K 9/46
USPC ........................................... 382/141
See application file for complete search history.

(56) References Cited

U.S. PATENT DOCUMENTS

2006/0093689 A1*   5/2006   Kawada ................... A61K 8/63
                                         424/771
2006/0233738 A1*   10/2006   Miyata .................. A23L 1/3002
                                         424/74
2012/0283112 A1*   11/2012   Binder ..................... G06F 19/18
                                         506/8

FOREIGN PATENT DOCUMENTS

JP      11-169453 A     6/1999
JP      2004-163405 A     6/2004
(Continued)

*Primary Examiner* — Ruiping Li
(74) *Attorney, Agent, or Firm* — Foley & Lardner LLP

(57) ABSTRACT

The purpose of the present invention is to provide a rapid and widely practicable cosmetic-evaluating method for evaluating the performance of candidate cosmetics in improving wrinkles in the horny cell layer. Provided is a method for evaluating the effectiveness in wrinkle improvement of a candidate cosmetic by immersing a horny-cell-layer sheet having creases and wrinkles in the candidate cosmetic, and verifying the disappearance of the creases and wrinkles after drying, whereby the purpose is achieved.

4 Claims, 2 Drawing Sheets

(51) Int. Cl.
    *G01N 33/50* (2006.01)
    *A61K 8/34* (2006.01)
    *A61K 8/365* (2006.01)
    *A61K 8/86* (2006.01)
    *A61Q 19/08* (2006.01)
    *G06K 9/46* (2006.01)
    *G06K 7/00* (2006.01)

(56) References Cited

FOREIGN PATENT DOCUMENTS

| | | |
|---|---|---|
| JP | 2010-119428 A | 6/2010 |
| JP | 2011-232290 A | 11/2011 |
| JP | 2012-032287 A | 2/2012 |

* cited by examiner

METHOD FOR EVALUATING COSMETIC FOR EFFECTIVENESS IN IMPROVING WRINKLES

CROSS-REFERENCE TO RELATED APPLICATIONS

This application is a National Stage application of PCT/JP2013/056174, filed Mar. 6, 2013, which claims priority from Japanese application JP 2012-071065, filed Mar. 27, 2012.

TECHNICAL FIELD

The present invention relates to a method for evaluating a cosmetic. Preferably, the present invention relates to a method for evaluating a cosmetic for a wrinkle-ameliorating effect.

BACKGROUND ART

Wrinkles increase as a phenomenon of skin aging with increasing age, and from a cosmetic viewpoint there is highly increasing interest in preventing and improving wrinkles, especially in women. Wrinkles are largely classified as fine wrinkles formed as a result of reduced function of the epidermis including the stratum corneum, and large wrinkles (or "expression wrinkles") formed by reduced function of the dermis below the epidermis. Wrinkles formed by reduced function of the epidermis including the stratum corneum are caused primarily due to reduction in the moisture-retaining function of the epidermis as a result of aging, ultraviolet rays, low temperature, low humidity and the like. Wrinkles formed by reduced function of the dermis, on the other hand, are caused by increase in matrix metalloproteases (MMPs) as a result of aging and ultraviolet rays, as well as mechanical stress, leading to collapse of the elastic structure of the skin composed of collagen and elastin (PTL 1 and NPLs 1, 2 and 3). It is known that fine wrinkle grooves formed in the skin progress to large wrinkles by deeply carving the grooves (NPL 4), and therefore fine wrinkles and large wrinkles are intimately related with each other.

The fact that fine wrinkles tend to be formed in cold, dry climates has become commonly recognized by most people, and for prevention and amelioration of fine wrinkles, it is considered important to promote moisture retention by cosmetics, and especially cosmetic water, latexes, creams, essences and the like, as well as to increase humidification using humidifiers. Cosmetics, and particularly cosmetics containing humectants such as glycerin and hyaluronic acid, are used to promote moisture retention.

In the prior art, there have been known methods of screening for candidate substances that increase stratum corneum transparency by means of skin roughening models using dry epidermis (PTL 2), and methods of screening for candidate substances that improve or increase skin barrier function, by using changes in the structure of stratum corneum intercellular lipids as a measure (PTL 3). Such methods are used to screen for candidate substances that improve stratum corneum transparency and skin barrier function, but there has been no description of screening for candidate substances that ameliorate wrinkles.

CITATION LIST

Patent Literature

[PTL 1] Japanese Unexamined Patent Publication No. 2003-201229
[PTL 2] Japanese Unexamined Patent Publication No. 2010-172200
[PTL 3] Japanese Unexamined Patent Publication No. 2010-175264
[PTL 4] Japanese Unexamined Patent Publication No. 2010-119428

Non-Patent Literature

[NPL 1] Arch Dermatol Res (2002)294:405-410
[NPL 2] Cell Motil Cytoskeleton 2000 January; 45(1):1-9
[NPL 3] Matrix Biol. 2001 November; 20 (7):397-406
[NPL 4] Skin Research and Technology 2011; 17:135-140

DISCLOSURE OF THE INVENTION

Problems to be Solved by the Invention

There is a desire to develop cosmetics that can repair wrinkles formed in the stratum corneum, and there is a need for an evaluation method for cosmetics that can determine the ability of candidate cosmetics to ameliorate stratum corneum wrinkles, in a rapid manner on a large scale.

Means for Solving the Problems

The present inventors have conducted diligent research on the mechanism of formation of fine wrinkles that develop due to reduced function of the epidermis including the stratum corneum, and have found that established fine wrinkles are formed when the grooves of non-established stratum corneal wrinkles (defined as "residual wrinkles" throughout the present specification), which are formed by reduced function of the stratum corneum and by movement of muscles under the skin continue for long periods without being sufficiently restored by bathing or by moisture retention using cosmetics (FIG. 1). Specifically, it was found that non-established residual wrinkles formed in the stratum corneum are a tendency to fold in the stratum corneum which is especially hard in the skin, and that epidermal fine wrinkles that are deeper than residual wrinkles form when the grooves of the hard stratum corneum are subjected to mechanical stress and become established as epidermal grooves.

Experience has demonstrated that fine wrinkles are formed by reduced function of the epidermis including the stratum corneum, and are produced primarily by winter dryness. Promoting adequate moisture retention using cosmetic water or latexes for fine wrinkles is known to be able to repair and ameliorate fine wrinkles, but once fine wrinkles become established to the epidermis further inward than the stratum corneum (to the granular layer, stratum spinosum and basal lamina), fine wrinkles may disappear temporarily with moisturization but reappear as time progresses. When such fine wrinkles established in the epidermis are allowed to remain, they can lead to formation of large wrinkles as structural changes of collagen and elastin take place in the dermis below the epidermis, and it is a known fact that repair of large wrinkles is difficult even with moisturization.

In the past, it has been vaguely recognized that fine wrinkles appearing with structural changes in the epidermis include moderate forms that can be repaired by moisturization and more advanced forms where the wrinkles only disappear temporarily by moisturization, and moisturization has been considered necessary for prevention of both forms, but there has not existed a suitable way of evaluating cosmetics that can repair fine wrinkles. Research by the present inventors has shown that among wrinkles associated with structural changes in the epidermis, the moderate forms that can be repaired by moisturization are the wrinkles where structural changes have occurred only in the stratum corneum (residual wrinkles), while more advanced forms that can only be temporarily repaired by moisturization are the wrinkles where structural changes have occurred not only in the stratum corneum but also in the epidermis including the granular layer, stratum spinosum and basal lamina (defined as "fine wrinkles" or "established fine wrinkles" throughout the present specification).

Residual wrinkles as defined in the present specification are not those associated with structural changes in the epidermis and dermis apart from the stratum corneum, but rather a state where folds have developed in the stratum corneum having reduced function due to drying, etc., by the movement of subcutaneous muscles. When such folds are allowed to remain, the folds produce mechanical stress and structural changes are created in the epidermis including the stratum corneum, and progress to established fine wrinkles. Fine wrinkles are known to progress to large wrinkles over long periods (NPL 4), and therefore in the field of cosmetic development, the development of cosmetics that can repair folds in the stratum corneum as residual wrinkles, was found to be important for preventing formation of established fine wrinkles, and therefore for preventing formation of large wrinkles. Since such cosmetics can release mechanical stress caused by residual wrinkles, continued administration of such cosmetics for long periods can exhibit effects of ameliorating fine wrinkles that have already been established in the epidermis and large wrinkles that have been established in the dermis.

Upon further research by the present inventors on residual wrinkles, it was surprisingly found that it is possible to model residual wrinkles by using a stratum corneum sheet. Specifically, it was found that when fold wrinkles have been created in a stratum corneum sheet, this truly models residual wrinkles in which folds have been formed in the stratum corneum by the movement of subcutaneous muscles, and therefore cosmetics that can satisfactorily repair such fold wrinkles can satisfactorily repair wrinkles and especially residual wrinkles, and thus can contribute to amelioration of established fine wrinkles and large wrinkles.

The present inventors have found that the degree of wrinkle improvement can be measured by contacting a stratum corneum sheet with fold wrinkles with a candidate cosmetic and drying it, and have invented a method for evaluating the wrinkle-ameliorating effects of candidate cosmetics.

More specifically, the present invention relates to the following.

(1) A method for evaluating a wrinkle-ameliorating effect of a candidate cosmetic, comprising:
forming fold wrinkles in a stratum corneum sheet;
immersing it in a candidate cosmetic;
drying it; and
measuring the degree of amelioration of the fold wrinkles of the stratum corneum sheet.

(2) The method according to (1), wherein measurement of the degree of amelioration of fold wrinkles is made by visual examination.

(3) The method according to (1), comprising a step of photographing the stratum corneum sheet before the immersing step in the candidate cosmetic and after the drying step.

(4) The method according to (3), wherein measurement of the degree of amelioration of fold wrinkles is made by image processing of the photographed stratum corneum sheet.

(5) The method according to any one of (1) to (4), wherein the wrinkle-ameliorating effect is an effect of ameliorating residual wrinkles.

Effect of the Invention

Conventionally, evaluation of wrinkles has required animal models or actual testing on human skin, which have been associated with individual differences, ethical issues and limits to testing frequency. According to the invention, a stratum corneum sheet can be used for evaluation of candidate cosmetics, and therefore homogeneous screening can be carried out on a large scale during product development, and therefore product development is facilitated.

BEST MODE FOR CARRYING OUT THE INVENTION

Figure 1:
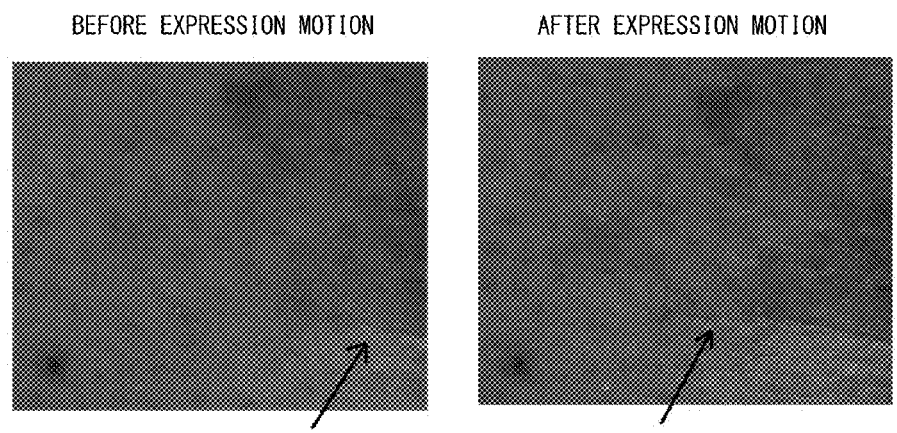
FIG. 1 is a pair of photographs showing formation of residual wrinkles in skin on a human face.

As a first aspect, the invention provides a method of evaluating the wrinkle-ameliorating effect of a candidate cosmetic. More specifically, the method of the invention comprises one or more steps selected from the group consisting of the following steps:
forming fold wrinkles in a stratum corneum sheet;
immersing it in a candidate cosmetic;
drying it; and
measuring the degree of amelioration of the fold wrinkles of the stratum corneum sheet.

A candidate cosmetic according to the invention is a cosmetic which has a possibility to exhibit an effect of ameliorating wrinkles. More specifically, a "candidate cosmetic" refers particularly to cosmetic water, latexes, creams and essences, but it also includes all products that are not directly for the purpose of improving skin but are to be applied onto skin, and for example, it includes sunscreens, insect repellents, allopecia agents, hair restorers, shaving lotions and after shave lotions. From the viewpoint of exhibiting a wrinkle-ameliorating effect by immersing and drying of a stratum corneum sheet, it is preferably an aqueous cosmetic such as cosmetic water or an essence.

A wrinkle-ameliorating effect is disappearance of wrinkles formed in skin. From the viewpoint of the present invention it is preferably disappearance or attenuation of residual wrinkles as the folds produced in the stratum corneum, but there is no limitation to this and instead it may be disappearance or attenuation of fine wrinkles associated with structural changes in the epidermis including the stratum corneum, and large wrinkles associated with structural changes in the dermis.

According to the invention, the stratum corneum sheet is a stratum corneum sheet prepared from live skin (prepared stratum corneum sheet) or a stratum corneum sheet obtained by cell culturing (cultured stratum corneum sheet), but it is preferably a cultured stratum corneum sheet, from the viewpoint of large-scale, uniform screening.

There are no particular restrictions on the source of a prepared stratum corneum sheet, but it is most preferably prepared from the stratum corneum of human skin. More specifically, it may be obtained by an invasive method such as surgical means.

A cultured stratum corneum sheet is a sheet of stratum corneum obtained by in vitro culturing, and the concept includes stratum corneum sheets isolated from sustained cultured skin tissue harvested from human skin, and stratum corneum sheets obtained from three-dimensionally cultured skin obtained by culturing fibroblasts, or fibroblasts differentiated in vitro from stem cells (for example, epithelial stem cells, embryonic stem cells or induced pluripotent stem cells), on a culture support composed of a polymer such as collagen, fibrin or polylactic acid, or a polysaccharide such as chitin, chitosan, chondroitin sulfate or hyaluronic acid. The stratum corneum sheet is isolated from culture-supported skin tissue using a method such as treatment with a protease in physiological saline having controlled calcium ion and magnesium ion concentrations. Three-dimensionally cultured skin that is used may be a human three-dimensional cultured epidermal model product commercially available from LabCyte EPI-MODEL (Japan Tissue Engineering). Because cultured stratum corneum sheets obtained from commercially available three-dimensional cultured epidermal model products have minimal differences between lots, different lots may be used to carry out the evaluation method of the invention, but in order to avoid differences between lots, a single cultured stratum corneum sheet may be cut into several sheet strips and used for the invention.

According to the invention, the stratum corneum sheet can be imparted with fold wrinkles by hand, but for consistent fold wrinkles, a plate with a hinge section may be used, to allow fold wrinkles to be formed by folding the plate at a fixed angle. Depending on the desired depth for the fold wrinkles, the angle may be selected as desired, and for example, it may be selected from among 30°, 45°, 60°, 75°, 90°, 120°, 135°, 150° and 180°.

According to the invention, the stratum corneum sheet is immersed in a candidate cosmetic in a temperature range in which cosmetics are commonly used. The immersing temperature is preferably set according to the locale where the candidate cosmetic is to be used, and for most purposes it is in the range of 10° C. to 40° C., preferably 15° C. to 30° C. and more preferably 20° C. to 30° C. The immersing time may be selected as desired, but a shorter immersing time will allow screening of candidate cosmetics with higher wrinkle-ameliorating power. The immersing time may be selected from among 10 seconds, 15 seconds, 30 seconds, 1 minute, 2 minutes, 3 minutes, 5 minutes, 10 minutes, 20 minutes, 30 minutes, 45 minutes, 1 hour, 1.5 hours, 2 hours and 3 hours, or a longer time such as 4 hours, 8 hours, 12 hours or 24 hours. When the candidate cosmetic is to be coated onto skin, the candidate cosmetic coated onto the skin will usually evaporate in a very short time, and therefore a relatively short immersing time of about 10 seconds to 2 minutes is selected. On the other hand, when the candidate cosmetic is to be applied using a pack or the like, a longer time, such as 10 minutes, 20 minutes, 30 minutes or overnight, is selected. Immersing refers to contact with the candidate cosmetic, and it may be a step of contacting the candidate cosmetic by dropping or coating.

Components that may be contained in candidate cosmetics include water and alcohols such as ethanol, glycerin and polyethylene glycol, as bases, amino acids such as glycine, betaine and Na pyrrolidonecarboxylate and saccharides such as fructose, maltitol, mannitol and trehalose, as humectants, glyceryl oleate, isostearylglyceryl and plant extracts, as surfactants, jojoba oil, camellia oil, olive oil, squalane and the like, as oils, hyaluronic acid, collagen, ceramide, ascorbic acid, vitamin E and the like, as active ingredients, sodium citrate, citric acid and sodium lactate as excipients, and benzoic acid salts and sorbic acid as antiseptic agents, but there is no limitation to these, and the cosmetic may contain any components that are commonly used in cosmetics.

According to the invention, the stratum corneum sheet that has been wetted with a candidate cosmetic by immersing is dried after the prescribed immersing time. The drying step may be carried out at any desired temperature and humidity, but preferably it is carried out at a temperature and humidity in which the candidate cosmetic is normally expected to be used. For example, the temperature and humidity will differ depending on the locale in which the candidate cosmetic is to be marketed, but they are independently selected in ranges of 10° C. to 40° C., preferably 15° C. to 30° C. and more preferably 20° C. to 30° C., and a humidity of 30% to 90%, preferably 40% to 80% and more preferably 50% to 60%. From the viewpoint of shortening the screening time, the drying step is preferably carried out at a higher temperature and/or a lower humidity than the temperature and humidity in which the candidate cosmetic is expected to be used.

Measurement of the degree of amelioration of fold wrinkles in the stratum corneum sheet is accomplished by visually evaluating the degree of disappearance of the fold wrinkles. For example, a standard solution such as a 10% glycerin water-soluble solution may be used, and based on the degree of disappearance of fold wrinkles after having conducted the step of adding fold wrinkles, the immersing step and the drying step under the same conditions, candidate cosmetics may be screened as having an excellent wrinkle-ameliorating effect if disappearance of fold wrinkles is exhibited that is equivalent to or greater than the standard. Conversely, if disappearance of fold wrinkles is not greater than the standard, the candidate cosmetic is judged to not have a wrinkle-ameliorating effect. Any desired solution may be selected as the standard solution, or any commercially available standard solution such as a cosmetic or essence may also be used.

Measurement of the degree of amelioration of fold wrinkles can also be evaluated by image processing of the degree of disappearance of fold wrinkles. For this method, the step of measuring the degree of amelioration of fold wrinkles may also include a step of photographing the stratum corneum sheet and a step of binary processing. Binary processing allows the degree of disappearance of fold wrinkles to be digitized, and therefore image processing evaluation is preferred from the viewpoint of allowing numerous candidate drugs to be screened with high throughput.

Concrete examples will now be provided for a more detailed explanation of the invention. However, the invention is in no way limited by the examples.

EXAMPLES

Example 1

Formation of Residual Wrinkles

After washing the face with soap, a single participant was conditioned for 10 to 30 minutes in an environmental chamber (temperature: 22° C. to 24° C., humidity: 10% to 45% RH), and after conditioning, wrinkles on the corner of the eye were photographed (FIG. 1, left). Next, an operation of firmly closing and opening the eyes was conducted 10 times, once very 5 seconds, as expression motion. The wrinkles on the corner of the eye were photographed immediately after expression motion (FIG. 1, right). As indicated by the arrows in FIG. 1, residual wrinkles extending from already existing large wrinkles were shown to be formed immediately after expression motion.

Example 2

Screening of Candidate Drug for Amelioration of Fold Wrinkles

Figure 2:
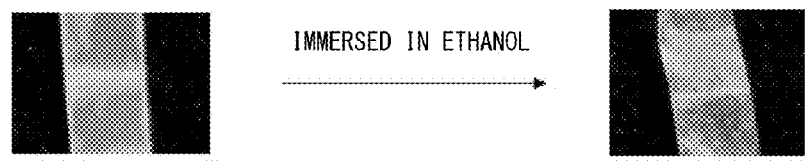
FIG. 2 is a set of photographs showing a wrinkle-ameliorating effect in a stratum corneum sheet wrinkle model.
Figure 2:
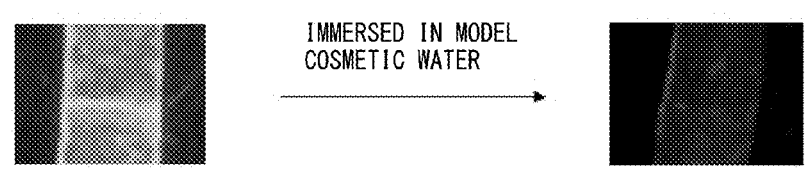

A human reconstituted epidermis model was purchased from Japan Tissue Engineering. This was subjected to trypsin treatment and the stratum corneum sheet was dried at 32° C., 60% humidity to obtain a transparent stratum corneum sheet. It was then folded at an angle of 90 degrees and restored to form a fold wrinkle in the stratum corneum sheet. The fold wrinkle section had lower stratum corneum transparency, and the damaged section was visualized (FIG. 2, at left). The fold-wrinkled stratum corneum sheet was used for evaluation of beautifying methods and cosmetics, as a model of residual wrinkles formed in the skin surface when skin is stretched by changes in expression. The fold-wrinkled stratum corneum sheet was immersed with model cosmetic water (10% glycerin, 3% ethyl alcohol, 0.3% HCO60 (polyethylene glycol (60) hydrogenated castor oil ether (product of Nikko Chemicals Co., Ltd.)), 0.09% sodium citrate, 0.01% citric acid) or ethanol for 30 minutes at room temperature (23° C.), and then dried at 32° C., 60% humidity for 18 hours, and a photograph was taken (FIG. 2). As a result, the model cosmetic water was more effective for repair of stratum corneum fold wrinkles.

Example 3

Figure 3:
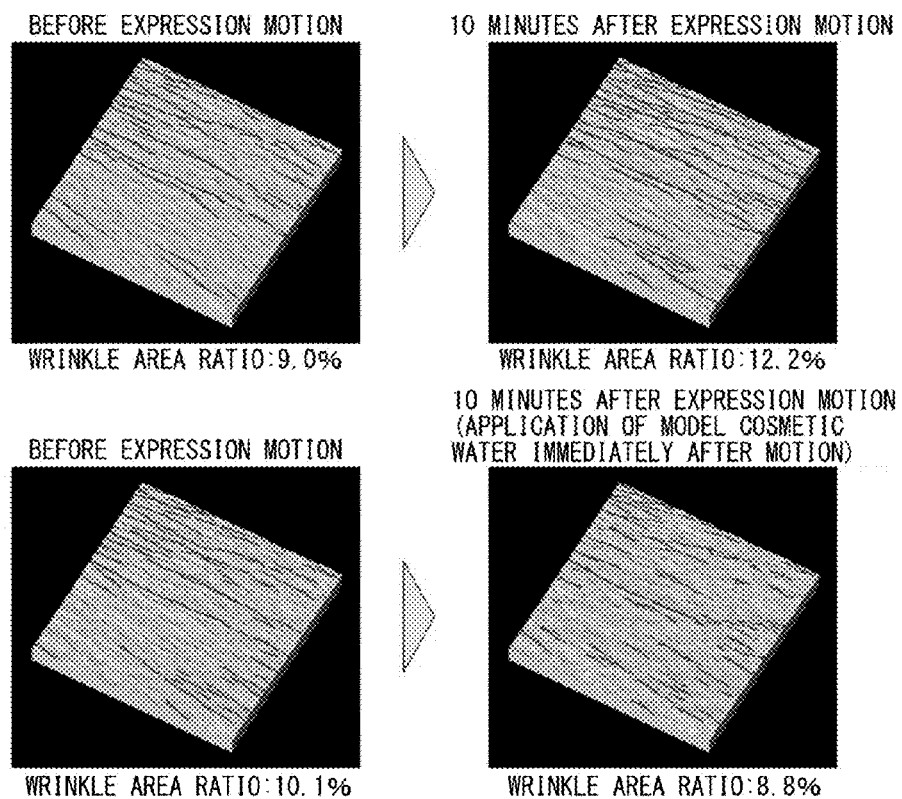
FIG. 3 is a set of photographs showing the state of a wrinkle before and after expression motion in vivo, in contrast with the state of a wrinkle after application of model cosmetic water immediately after expression motion.

Formation of Wrinkles by Expression Motion In Vivo, and Amelioration of Wrinkles by Application of Model Cosmetic Water After washing the face with soap, a single participant was conditioned for 10 to 30 minutes in an environmental chamber (temperature: 22° C. to 24° C., humidity: 10% to 45% RH), and immediately after conditioning, a skin replica was harvested by the method described. Next, expression motion (an operation of firmly closing the eyes several times) was carried out on the panel and a replica was then harvested. A model cosmetic water was then applied, and after 10 minutes a replica was harvested by the previous method. The harvested replica was subjected to three-dimensional image analysis using image analysis software prepared according to the method described in PTL 4, and the wrinkle area ratio was calculated. The results are shown in FIG. 3. This test demonstrated that residual wrinkles formed by expression motion can be ameliorated by application of model cosmetic water, as shown in the in vivo test, that a fold-wrinkled stratum corneum sheet adequately models residual wrinkles, and that cosmetics selected by a screening method for cosmetics or beautifying methods with a fold-wrinkled stratum corneum sheet according to the invention, can improve wrinkles in in vivo testing as well.

Thus, while it has normally been necessary to conduct monitoring tests using candidate cosmetics with several to several dozen monitored participants over several weeks in order to exam the ameliorating effects of cosmetics on wrinkles, using a fold-wrinkled stratum corneum sheet as a residual wrinkle model allows easy and convenient primary screening of candidate cosmetics with ameliorating effects on wrinkles.

The invention claimed is:

1. A method for evaluating a stratum corneal wrinkle-ameliorating effect of a candidate cosmetic, comprising:
    forming fold wrinkles in a cultured stratum corneum sheet;
    immersing the cultured stratum corneum sheet with fold wrinkles in a candidate cosmetic;
    drying the cultured stratum corneum sheet with fold wrinkles,
    photographing the cultured stratum corneum sheet with fold wrinkles to obtain an image of the photographed cultured sheet;
    image processing the image of the photographed cultured sheet to measure the degree of amelioration of the fold wrinkles of the cultured stratum corneum sheet.

2. The method according to claim 1, comprising a step of photographing the cultured sheet before the immersing step in the candidate cosmetic.

3. The method according to claim 1, wherein the wrinkle-ameliorating effect is an effect of ameliorating residual wrinkles.

4. The method according to claim 1, wherein the image processing step is carried out by binary processing.

* * * * *